United States Patent

Bloedau et al.

[19]

[11] Patent Number: 5,860,943
[45] Date of Patent: Jan. 19, 1999

[54] ABDUCTOR HINGE FOR A HIP STABILIZER AND METHOD OF ADJUSTING THE SAME

[75] Inventors: Clarence R. Bloedau; Jack E. Ball, both of Ft. Worth, Tex.

[73] Assignee: Restorative Care of America Incorporated, Clearwater, Fla.

[21] Appl. No.: 57,854

[22] Filed: Apr. 6, 1998

[51] Int. Cl.$^6$ .................................................. A61F 5/00
[52] U.S. Cl. ............................... 602/16; 602/24; 16/354
[58] Field of Search .................. 602/5, 16, 24, 602/26, 23; 16/328–332, 354

[56] References Cited

U.S. PATENT DOCUMENTS

| | | | |
|---|---|---|---|
| 3,732,861 | 5/1973 | Lehneis | 602/16 X |
| 4,463,751 | 8/1984 | Bledsoe | 602/16 |
| 4,520,804 | 6/1985 | DiGeorge | 602/16 |
| 4,738,252 | 4/1988 | Friddle et al. | 602/16 X |
| 4,982,732 | 1/1991 | Morris | 602/26 |
| 5,052,379 | 10/1991 | Airy et al. | 602/16 |

*Primary Examiner*—Linda C. M. Dvorak
*Attorney, Agent, or Firm*—Zarley, McKee, Thomte, Voorhees & Sease

[57] ABSTRACT

The hip abductor hinge for a hip stabilizer includes a top, middle and bottom connector with hubs and circular apertures that engage a locking device. The bottom and middle hubs have splines on the interior portion of the hubs. The locking device has splines on the exterior portion and interlock with the splines of the bottom and middle connector. The locking device also has a threaded central bore which extends from the interior portion of the locking device through the circular aperture of the top connector. A screw extends through the circular apertures and the threaded central bore. The position of the middle connector can be adjusted by rotating the screw such that the locking device disengages with the bottom circular aperture, rotating the middle connector, and then rotating the screw such that the locking device reengages with the bottom circular aperture.

6 Claims, 4 Drawing Sheets

ABDUCTOR HINGE FOR A HIP STABILIZER AND METHOD OF ADJUSTING THE SAME

BACKGROUND OF THE INVENTION

After hip surgery it is desirable to control the degree of hip abduction. Likewise, for some congenital hip defects and hip dislocations, abduction is also necessary. A benefit of some hip abductors is the capability of adjustment to accommodate varying degrees of abduction. Hip stabilizers are well known in the art and some include adjustable hip abductors. However, such prior art devices are not capable of convenient and quick adjustment with a precise degree of measurement.

Therefore, a primary objective of the present invention is to provide an improved abductor hinge for a hip stabilizer.

A further objective of the present invention is the provision of a hip abductor device which allows for a precise degree of adjustment.

A still further objective of the present invention is the provision of a hip abductor device which can be adjusted with a minimum degree of difficulty.

A further objective of the present invention is the provision of a hip abductor device which is quick and easy to place and adjust on the patient, comfortable to wear, durable in use, and economical to manufacture.

These and other objectives will become apparent from the following description of the invention.

SUMMARY OF THE INVENTION

The hip abductor hinge includes a top, middle and bottom connector, a locking device, and a screw. The connectors each have a hub with a circular aperture that run perpendicular to the connector. The middle and the bottom connectors both have splines on the interior portion of the hub. The locking device has splines on the exterior portion and a threaded center bore which extends from the interior portion. The splines on the locking device interlock with the splines on the bottom connector and the locking device extends above the bottom hub to connect with the splines of the middle connector. The threaded center bore extends through the circular aperture of the top connector. The screw extends through the circular aperture of the top connector, the threaded center bore of the locking device, the middle and bottom circular apertures.

The top connector extends downwardly from the hub and bore and the bottom connector extends upwardly from the hub and bore such that they are aligned vertically. Both connectors have bores that when aligned with the bores from an extending member of the hip stabilizer can be attached with a screw. The middle connector extends in an opposite direction from the top and bottom connector and also has bores which when aligned with the bores of a member from the hip stabilizer can be attached with screws. When assembled the middle connector is locked in place. The middle connector can be adjusted by turning the screw such that the locking device is lifted above the splines of the bottom connector. Each spline of the middle connector represents an adjustment of one degree in relation to a spline of the bottom connector.

DETAILED DESCRIPTION OF THE PREFERRED EMBODIMENT

Figure 1:
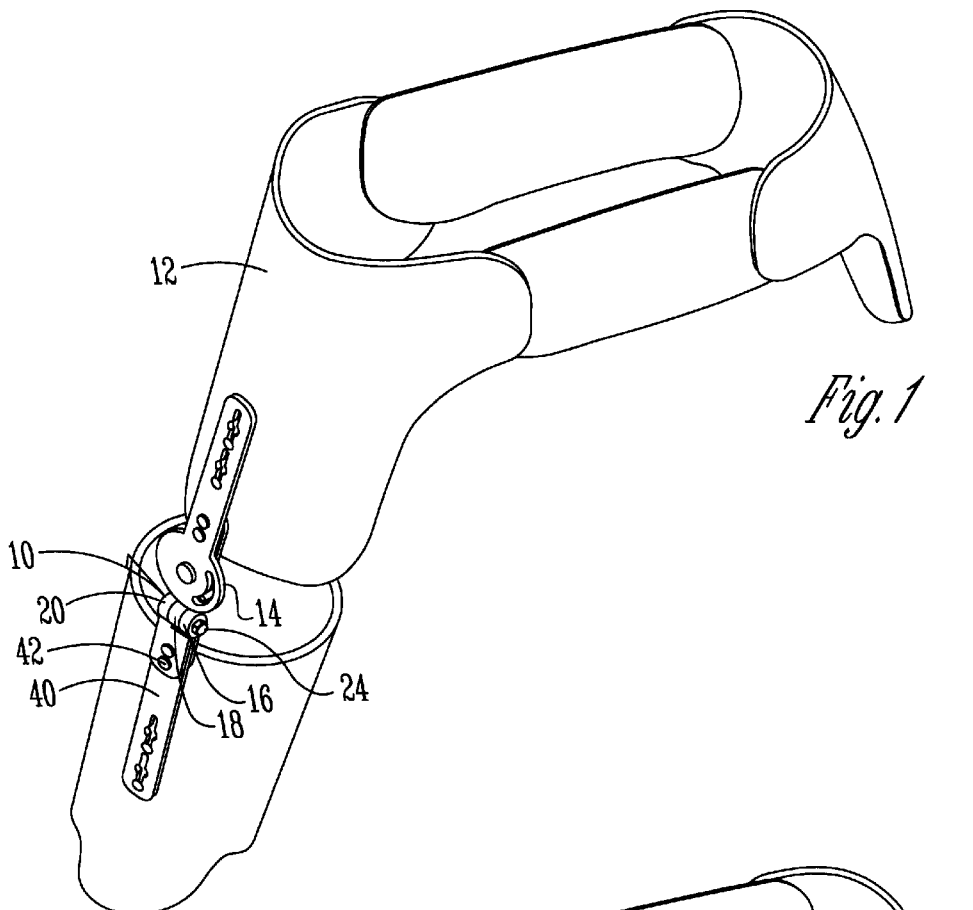
FIG. 1 is a perspective view of the hip abductor hinge attached to a hip stabilizer.
Figure 2:
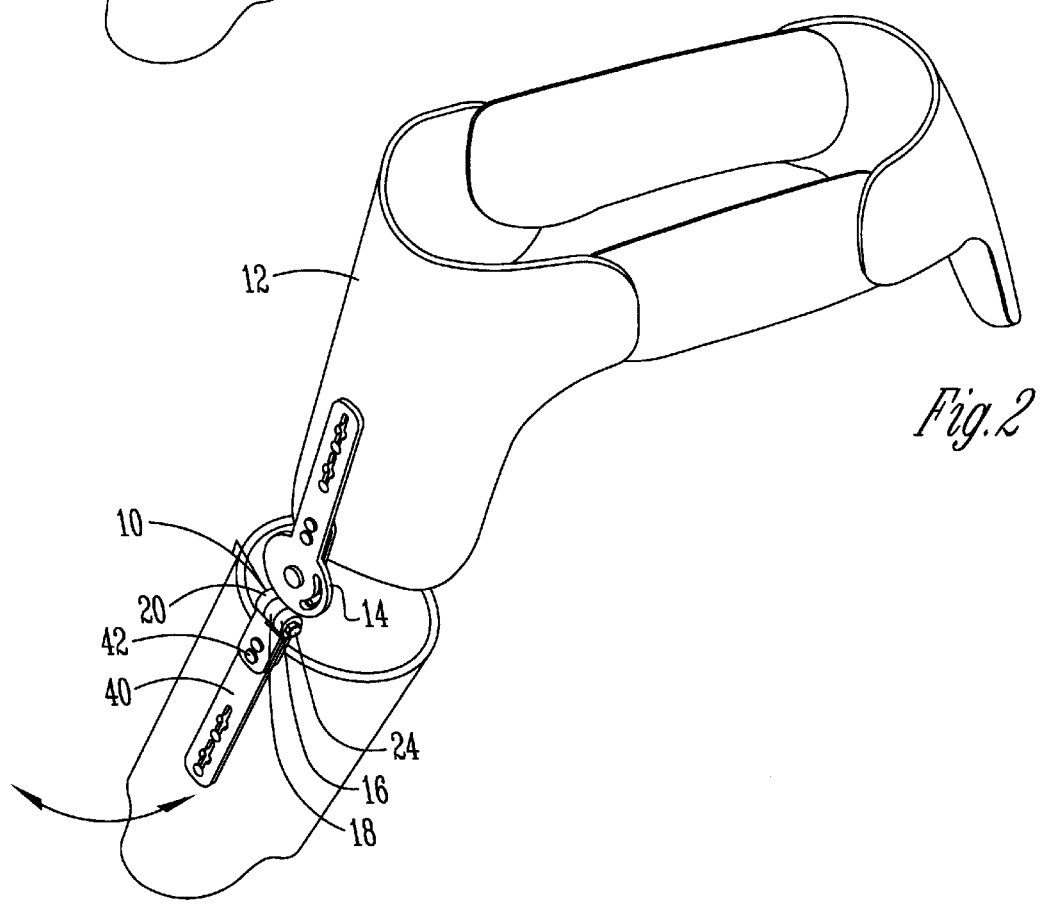
FIG. 2 is a perspective view of the hip abductor hinge attached to a hip stabilizer and extended in an outward position.
Figure 3:
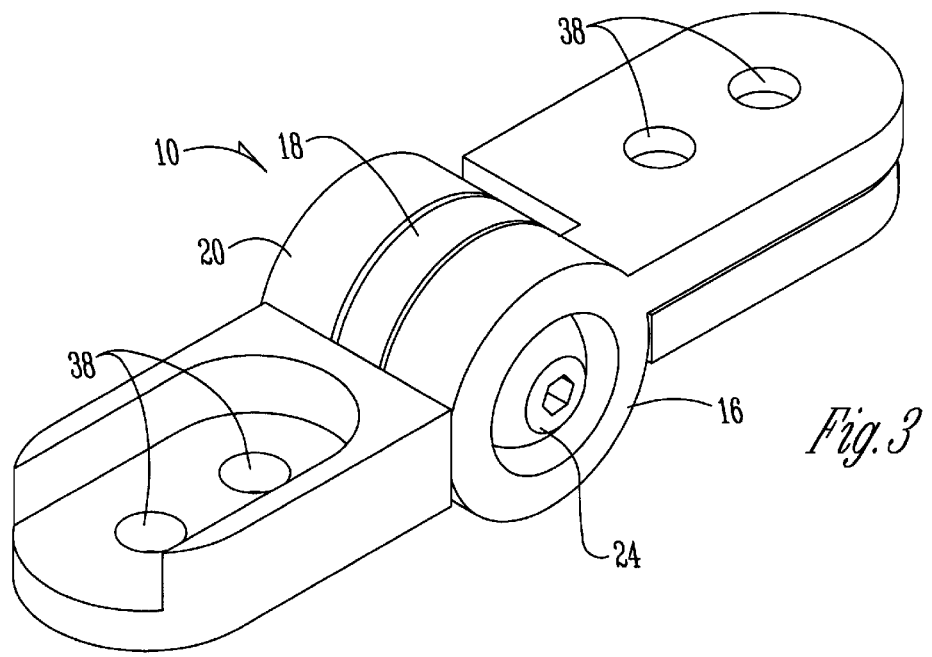
FIG. 3 is a perspective view of the hip abductor hinge completely assembled.
Figure 4:
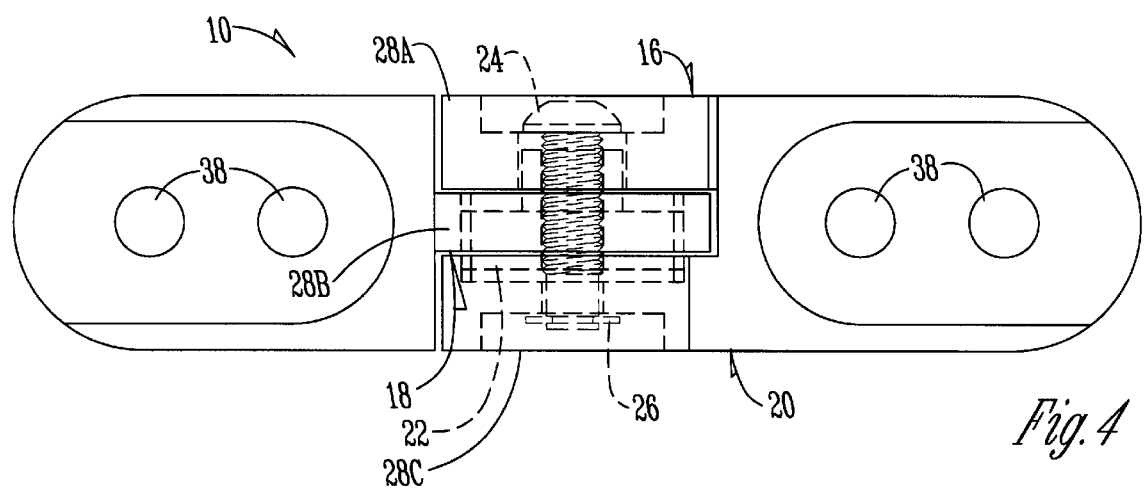
FIG. 4 is a side elevational view of the hip abductor hinge completely assembled.
Figure 5:
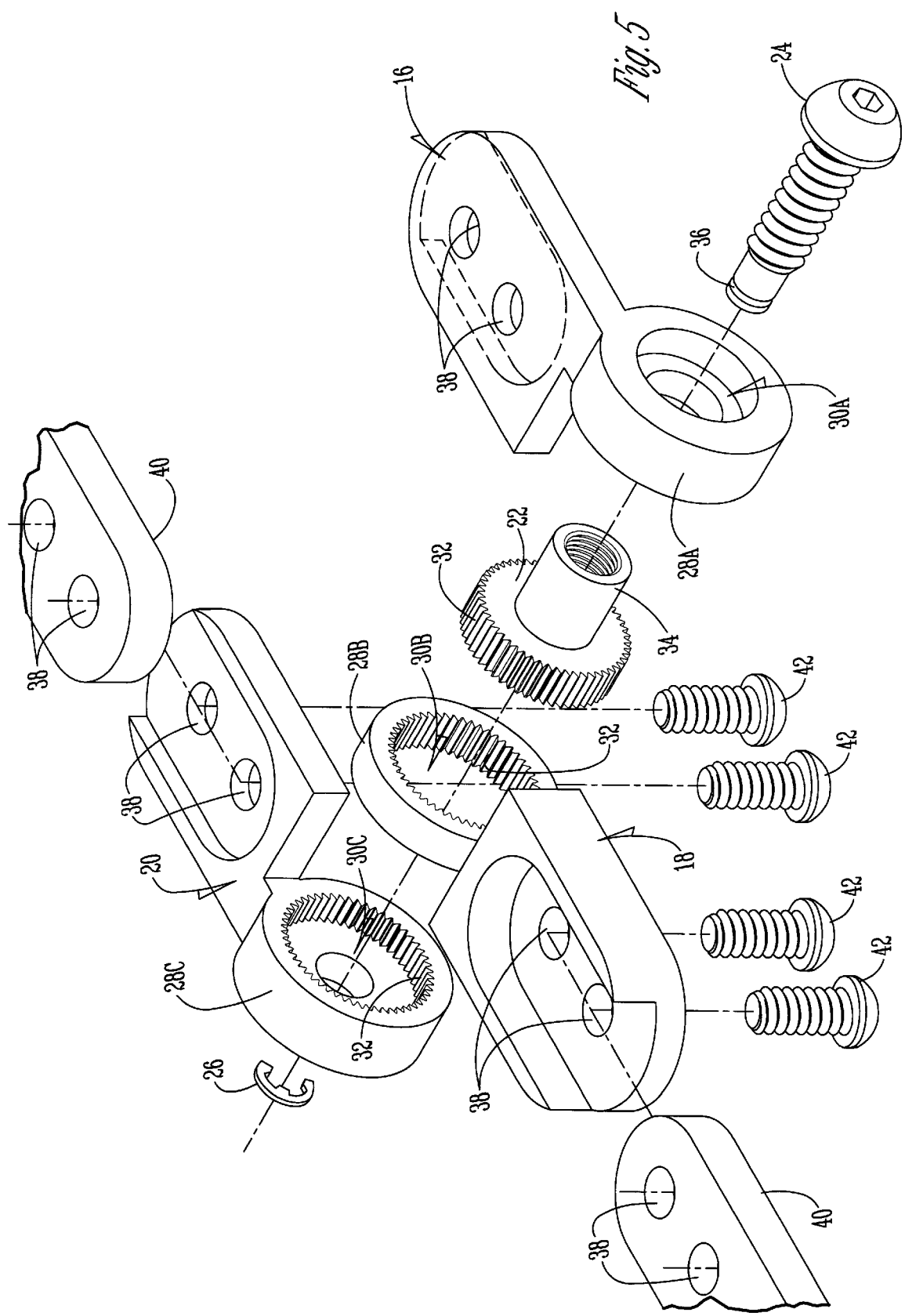
FIG. 5 is a perspective view of the hip abductor hinge.
Figure 6:
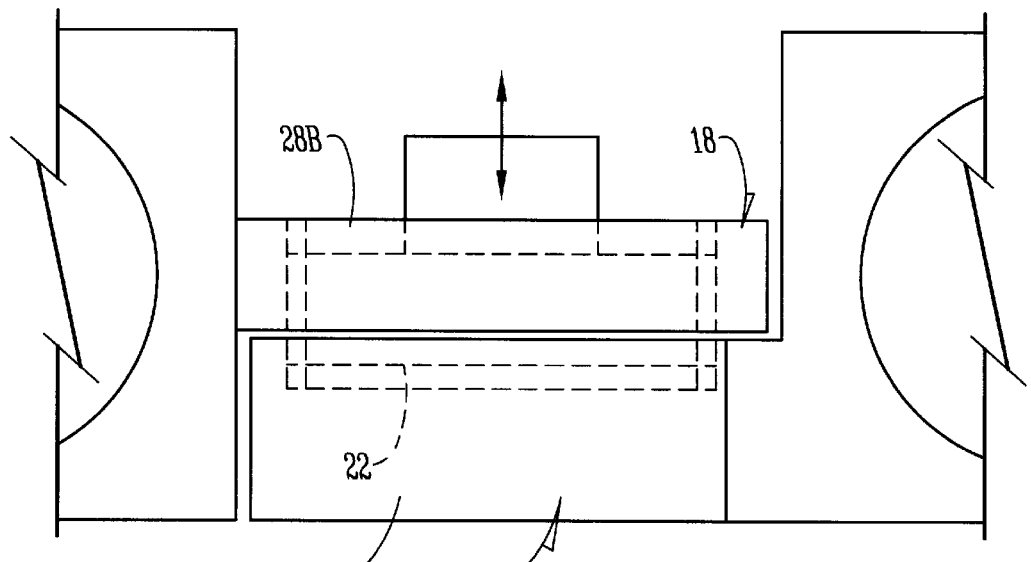
FIG. 6 is a side elevational view of the locking device while engaged.
Figure 7:
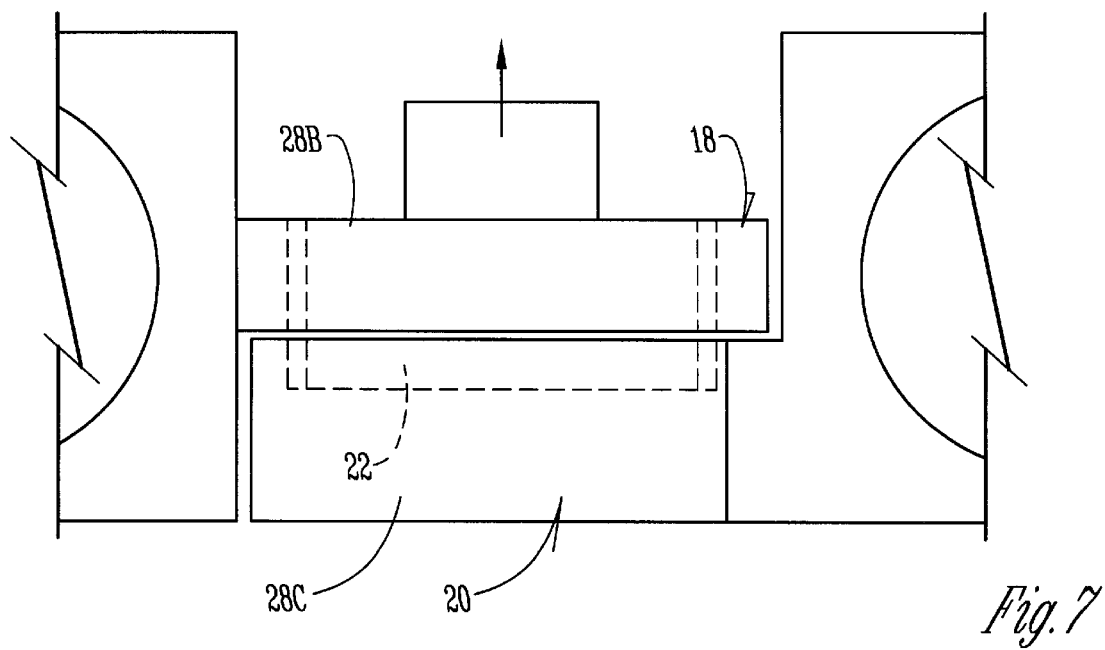
FIG. 7 is a side elevational view of the locking device when not engaged.

The hip abductor hinge of the present invention is generally designated by the reference numeral 10 in the drawings. As shown in FIGS. 1 and 2, the abductor hinge 10 is attached to a hip stabilizer 12 and a flexion hinge 14 which is drawn in but does not constitute a part of this invention. The abductor hinge 10 includes a top connector 16, a middle connector 18, a bottom connector 20, a locking device 22, a screw 24, and a snap washer 26. The top 16, middle 18, and bottom connector 20 each has a hub 28A, B, C which is juxtapositioned with respect to each other and aligned perpendicular to the applicable connector. Each hub 28 has a circular aperture 30A, B, C. The middle hub 28B and the bottom hub 28C have splines 32 on the interior portion of the hub 28. The locking device 22 has splines 32 on the exterior portion. The splines 32 of the locking device 22 fit within and interlock with the splines 32 of the bottom hub 28C, and extend to interlock with the splines 32 of the middle hub 28B as shown in FIG. 6. A hollow threaded central bore 34 extends from the interior portion of the locking device 22 through the circular aperture 30A of the top hub 28A. The screw 24 extends through the top circular aperture 30A, the threaded central bore 34, the middle circular aperture 30B and the bottom circular aperture 30C. The screw annular groove 36 near the tip. The snap washer 26 fits around the annular groove 36 to prevent the screw 24 from working loose.

Each connector has connecting bores 38 which are used to attach the hinge to the hip stabilizer 12. The top connector 16 extends downward from the hub 28A and the bottom connector 20 extends upward from the hub 28C such that when the connecting bores 38 are aligned the top 16 and bottom connector 20 are in vertical alignment. An extending member 40 from the hip stabilizer 12 can fit between the top 16 and bottom connector 20 and is secured by an assembly screw 42 that runs through the aligned connecting bores 38. The middle connector 18 can be attached to a member 40 from the hip stabilizer 12 by aligning the bores in the member with the connecting bores 38 and extending assembly screw 42 through the aligned connecting bores 38.

Each spline 32 represents one degree of adjustment in relation to the splines 32, of a corresponding connector. When assembled the middle connector 18 is locked in position. To adjust the position of the middle connector 18 the screw 24 is rotated such that the locking device 22 disengages with the circular aperture 30C of the bottom connector 20. The middle connector 18 can then be freely rotated. To relock the middle connector 18 the screw 24 is rotated such that the locking device 22 reengages with the bottom connector 20 where the splines 32 of the bottom connector 20 and the locking device 22 interlock as shown in FIG. 6.

The invention has been shown and described above in connection with the preferred embodiment, and it is understood that many modifications, substitutions and additions may be made which are within the intended broad scope of the invention. From the foregoing, it can be seen that the present invention accomplishes at least all of the stated objectives.

What is claimed is:

1. An improved hip abductor hinge for a hip stabilizer, comprising:

top, middle and bottom connectors juxtapositioned with respect to each other, a hub element on each connector, circular apertures in each hub element and being in alignment with each other, splines in the apertures of the hub elements on said middle and bottom connectors, a locking element having a circular splined portion slidably mounted in the splined apertures of the hub elements of said middle and bottom connectors, and having a threaded center bore in axial alignment with said apertures, a threaded screw extending through said center bore, releasable means on said screw for holding it against longitudinal movement, said screw adapted to be rotated to move said locking element back and forth between a locking position wherein the circular splined portion thereof engages both the splines in apertures in the hubs of said bottom and middle connectors, to an unlocked hinged position wherein the circular splined portion engages only the splines in the apertures of the hub of said middle connector element.

2. The device of claim 1 wherein the splines are positioned such that the rotational movement of one spline in said bottom connector with respect to a spline in the middle connector represents an adjustment of one degree between said bottom and middle connectors.

3. The device of claim 1 wherein a lock means is on said screw for releasably holding the same against longitudinal movement with respect to said connectors.

4. The device of claim 1 wherein said bottom and top connectors are in alignment with each other to facilitate connection thereof to a hip abductor.

5. A method of locking and unlocking a hip abductor hinge which has top, middle and bottom connectors juxtapositioned with respect to each other, a hub element on each connector, circular apertures in each hub element and being in alignment with each other, splines in the apertures of the hub elements on said middle and bottom connectors, a locking element having a circular splined portion slidably mounted in the splined apertures of the hub elements of said middle and bottom connectors, and having a threaded center bore in axial alignment with said apertures, a threaded screw extending through said center bore, releasable means on said screw for holding it against longitudinal movement, comprising, releasing said screw for longitudinal movement, rotating said screw to move said locking element back and forth between a locking position wherein the circular splined portion thereof engages both the splines in apertures in the hubs of said bottom and middle connectors, to an unlocked hinged position wherein the circular splined portion engages only the splines in the apertures of the hub of said middle connector element.

6. The method of claim 5 wherein said screw is released for longitudinal movement, sliding said locking device out of engagement with said bottom connector, rotating said bottom connector with respect to said middle connector, and slidably reengaging said locking device with said bottom connector without disengaging said locking device with said middle connector, and holding said screw adjacent longitudinal movement.

* * * * *